United States Patent

Bukta

[11] Patent Number: 5,611,337
[45] Date of Patent: Mar. 18, 1997

[54] PULSOXIMETRY EAR SENSOR

[75] Inventor: Anton Bukta, Sindelfingen, Germany

[73] Assignee: Hewlett-Packard Company, Palo Alto, Calif.

[21] Appl. No.: 430,734

[22] Filed: Apr. 28, 1995

[30] Foreign Application Priority Data

Jul. 6, 1994 [DE] Germany ........................ 44 23 597.6

[51] Int. Cl.$^6$ ........................................ A61B 5/00
[52] U.S. Cl. .................................. 128/633; 356/39
[58] Field of Search ........................ 128/632, 633, 128/637, 644, 664–7; 24/530, 545, 570, 531; 356/39–41

[56] References Cited

U.S. PATENT DOCUMENTS 4,685,464 8/1987 Goldberger et al. .

FOREIGN PATENT DOCUMENTS

| 2063691 | 9/1992 | Canada ........................... 128/633 |
| 572684A1 | 12/1993 | European Pat. Off. . |
| 572684 | 12/1993 | European Pat. Off. ........ 128/633 |
| 3703458 | 8/1991 | Germany . |
| 49312 | 12/1993 | Germany ........................ 128/633 |

Primary Examiner—Angela D. Sykes
Assistant Examiner—Bryan K. Yarnell

[57] ABSTRACT

A one-piece injection molded elastic plastic peg-like or clip-like support for sensor elements of a pulsoximetry ear sensor has legs interconnected by an elastically deformable rib. The rib runs in the longitudinal direction of a web and projects from a web surface. The smooth surfaces enable the support to be easily cleaned and sterilized and inexpensively manufactured.

13 Claims, 2 Drawing Sheets

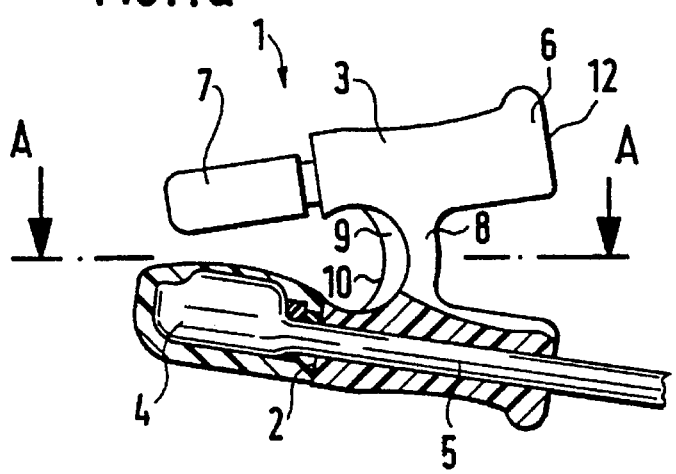
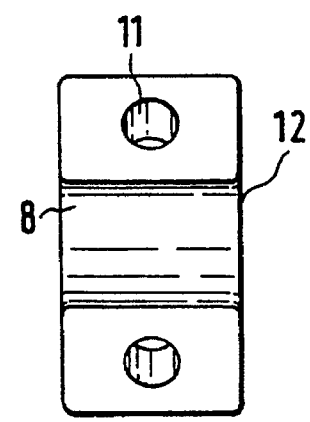
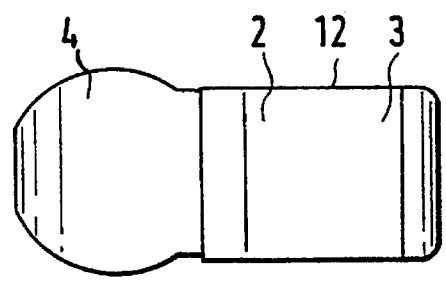
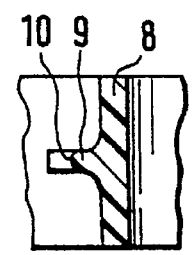
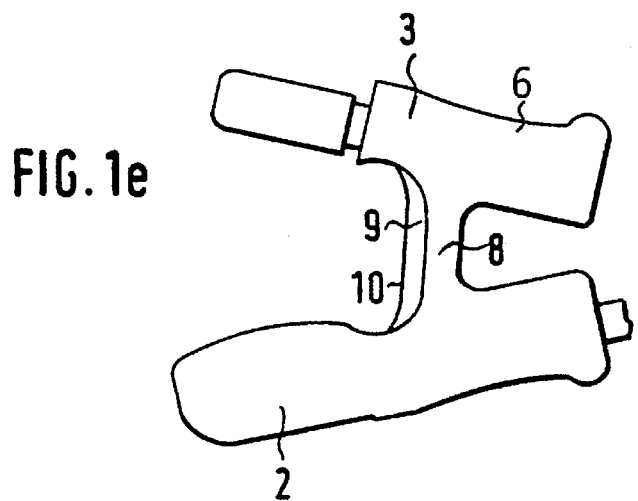

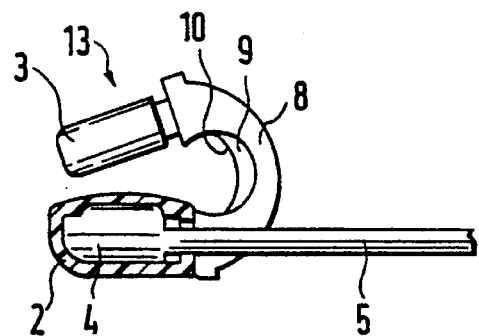
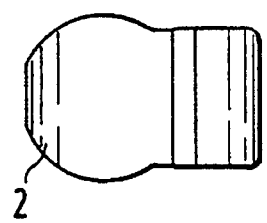
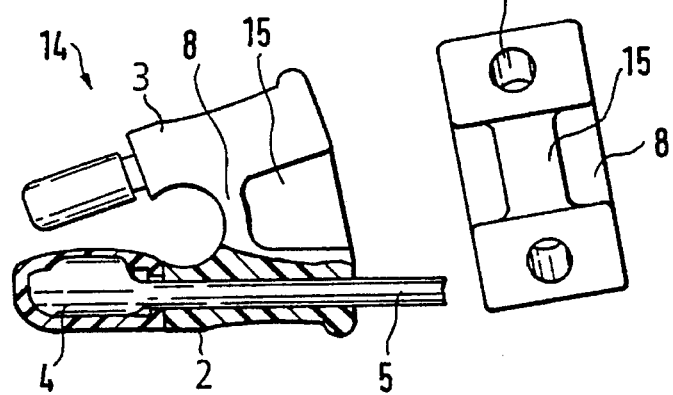
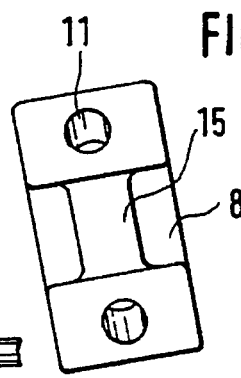
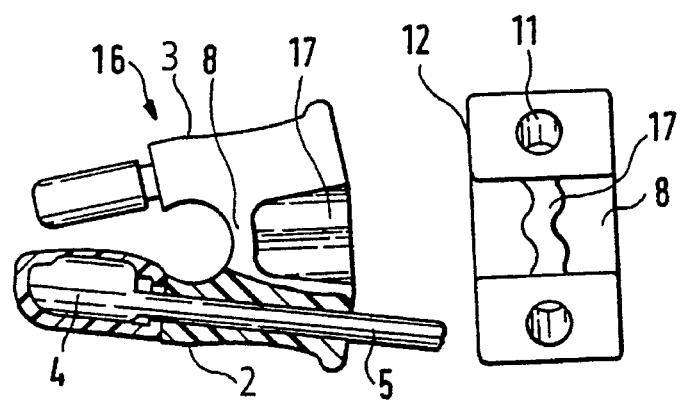
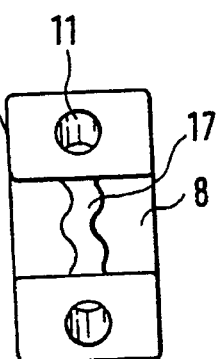

PULSOXIMETRY EAR SENSOR

BACKGROUND OF THE INVENTION

The present invention relates to a pulsoximetry ear sensor structure for measuring the oxygen saturation in the blood of a patient.

In a known, standard non-invasive method of blood pulsoximetry, light with at least two wavelengths is beamed into the tissue of a patient. Conclusions are drawn concerning the oxygen saturation from the attenuation of the alternating component of the reflected or transmitted signal. Typically light-emitting diodes and photocells are mounted on a sensor structure for this purpose. The ear lobe is a body part which is particularly suitable for the measurement. Photovoltaic cells can be applied closely and without any tilting to the ear lobe skin, so that the signal alternating component, which is smaller by an order of magnitude than the signal constant component, can be determined in an optimum manner.

In the hitherto known ear sensor structures the sensor elements are fixed to a support, which in much the same way as two legs of a clothes, pin are interconnected by a spring clip. The spring clip applies a spring tension to the legs as is necessary for fixing the sensor structure to the ear lobe. The spring clip must be separately fitted for this purpose. U.S. Pat. No. 4,685,464 discloses a similar sensor structure for measurements on a figure. Such sensor structures, which require an additional spring, are difficult to clean, because the clip causes the sensor structure to have numerous dirty edges which are difficult to access. In addition, a separate fitting of the spring clip is necessary.

An object of the present invention is to provide a new and improved pulsoximetry ear sensor structure.

SUMMARY OF THE INVENTION

According to the invention this object is achieved by a pulsoximetry ear sensor having the features of the main claim. In particular, the pulsoximetry ear sensor according to the invention has a one-piece support for the sensor elements made from an elastic plastics material. The one-piece pulsoximetry ear sensor has two legs, which can receive the sensor elements at their ends. The legs are interconnected by means of an elastically deformable web having at least one rib passing in the web longitudinal direction and projecting out of the web surface. The web and legs are arranged, so that there is a support similar to either an ear clip or a peg. The deformable rib, as a result of its tension, fulfils the function of a clip. It pulls or pushes, as a function of the arrangement of the rib on the web, the leg ends together. Thus, the rib provides the necessary contact pressure to assure that the ear sensor is held on the ear lobe. For an ear sensor formed as a clip the ends are bent apart and then fixed to the ear. For a support formed as a peg, compression of the leg ends remote from the sensor elements provides the necessary expansion or spreading to fix the ear sensor to the ear lobe. In the case of a peg-like support, it is possible to place the rib projecting out of the web either on one or other side of the web.

A pulsoximetry ear sensor constructed in this way is robust and, due to its flat surfaces, easy to clean and disinfect. As a result of the one-piece injection moulding manufacture there is only installation work with respect to the insertion of the sensor elements.

Further advantageous developments can be gathered from the subclaims. According to a preferred embodiment the pulsoximetry ear sensor has a peg-like construction, so that the web subdivides the legs into an operating area and a clamping area, on whose end the sensor elements are arranged. This simplifies the handling of the ear sensor, because compressing the ends of the leg in the operating area results in opposite ends of the support having spread apart and consequently can easily be fixed to the ear lobe. The contact pressure is determined by the rib projection from the web and one or more ribs can in fact be provided.

In one embodiment a rib is placed on the side of the web facing the sensor elements a rib is preferably designed in such a way that the upper edge is crescent-shaped when the leg is closed. On spreading the clamping area the upper edge of the web is stretched, so that it can run parallel to the web in the case of maximum spreading.

In another advantageous embodiment of a peg-like support the rib is located in the operating area, so that on pressing together the operating area for spreading the clamping area the rib is squeezed. As a result of the rib elasticity, release of the rib leads to a pressing apart of the legs in the vicinity of the operating area to bring about the necessary contact pressure. The rib can have a corrugated, i.e. wavy, cross-section.

The support material is preferably a polyurethane elastomer or silicone. The material hardness range is appropriately between 98 and 75 Shore A.

DESCRIPTION OF THE DRAWINGS

The invention is described in greater detail hereinafter relative to embodiments and the attached drawings, wherein show:

FIGS. 1A–1E are different views of a peg-like ear sensor with a crescent-shaped rib.

FIGS. 2A and 2B are different views of another embodiment with a clip-like ear sensor.

FIGS. 3A and 3B are different views of a peg-like ear sensor with a rib in the operating area, FIGS. 4A and 4B are different views of another ear sensor according to FIG. 3 in which the rib has a corrugated or wavy construction.

DETAILED DESCRIPTION OF THE EMBODIMENTS

FIG. 1a is a side view of a peg-like pulsoximetry ear sensor 1, in which a leg 2 together with a sensor element 4 and a connecting cable 5 are shown in section. The two legs 2 and 3 are subdivided into an operating area 6 and a clamping area 7, which are defined by the spatial fitting of the web 8 connecting the two legs. On the side facing the sensor elements 4 the web 8 carries a rib 9 which, as a result of its tension, draws together the ends of the legs 2, 3 having the sensor elements and therefore ensures the necessary contact pressure on the ear lobe. The ear sensor is shown in FIG. 1a in its inoperative position. As shown in FIG. 1e the sensor ear is clamped to the ear lobe by pressing down on operating area 6 to deform web 8 is deformed and tension the upper edge 10 of the rib 9. The upper edge 10 of the rib 9 then runs substantially parallel to the web 8. Following the spreading of the legs 2 and 3 in the clamping area 7 the resilience of the rib 9 ensures the necessary contact pressure on the ear lobe. The contact pressure is set in such a way that an adequate blood flow through the ear lobe is ensured.

FIG. 1b is a front view of the ear sensor 1 with the end face of the legs 2, 3 and the openings 11 for the connecting cable 5 of the sensor elements. The sensor elements can either be subsequently inserted in the provided slits in the support 12 or can be injection moulded in at the time of manufacture. For this purpose the sensor element is connected firmly and in water-tight manner to the connecting cable beforehand.

FIG. 1c is a sectional view through the web 8 along line A—A with the rib 9.

FIG. 1d is a plan view of the leg 2.

FIGS. 2a and 2b are side and bottom views of another embodiment of a pulsoximetry ear sensor 13, which has a clip-like construction. As in FIG. 1a, FIG. 2a includes a sectional view of a leg in section and the ear sensor in the inoperative position. The ear sensor 13 also has a web 8 with a crescent-shaped rib 9. FIG. 2b is a plan view of the leg 2.

FIGS. 3a and 3b are side and front views of a peg-like pulsoximetry ear sensor 14 in a part sectional view as in FIG. 1. The sensor of FIGS. 3a and b differs from the ear sensor of FIGS. 1a–1e by including a rib 15 between the operating areas 6 of the legs 2 and 3. FIG. 3b is the front view of the sensor 14.

FIG. 4a is a partial sectional side view of another embodiment with a corrugated or wavy rib 17 between the legs 2 and 3. FIG. 4b is a front view of the structure shown in FIG. 4a.

The pulsoximetry ear sensors explained hereinbefore in conjunction with the drawings all have a one-piece support 12 produced by injection moulding from a polyurethane elastomer or silicone. The material hardness range is between 98 and 75 Shore A. As a result of the special design of the material and the rib 9, the contact pressure necessary for fixing the sensor to the ear lobe is obtained. As has already been mentioned, the sensor elements 4 are firmly moulded with the connecting cable and are then either moulded in at the time of producing the support 12 (as shown in the drawings) or are subsequently inserted in the provided recess and a slit for the connecting cable 5, in which the sensor element with the cable is securely held due to the elasticity of the material.

I claim:

1. Pulsoximetry ear sensor structure comprising a one-piece, elastic plastic support for a sensor element, the support including a pair of legs that are normally urged toward each other and selectively spread apart, the legs being interconnected to each other by an elastically deformable web extending in a longitudinal direction generally between the legs, the web having a surface and at least one elastically deformable rib extending in the web longitudinal direction and projecting from the web surface.

2. Pulsoximetry ear sensor structure according to claim 1 wherein the web subdivides the legs into an operating area and a clamping area, the clamping area including the sensor element.

3. Pulsoximetry ear sensor structure according to claim 2 wherein the rib is located on a side of the web facing the sensor element, the rib having an upper edge forming a crescent when the ends of the legs are normally urged toward each other.

4. Pulsoximetry ear sensor structure according to claim 3 wherein the rib, web, legs and upper edge are constructed and arranged so that when the legs are spread apart by a maximum amount the upper edge of the rib is substantially parallel to the web.

5. Pulsoximetry ear sensor structure according to claim 2 wherein the rib is located in the operating area.

6. Pulsoximetry ear sensor structure according to claim 5 wherein the rib has a wavy cross-section.

7. Pulsoximetry ear sensor structure according to claim 1 wherein the support is made of a polyurethane elastomer.

8. Pulsoximetry ear sensor structure according to claim 1 wherein a material used to make the support has a material hardness range between 98 and 75 Shore A.

9. Pulsoximetry ear sensor structure according to claim 1 wherein the support is made of silicone.

10. Pulsoximetry ear sensor structure according to claim 9 wherein the web subdivides the legs into an operating area and a clamping area, the clamping area including the sensor element.

11. Pulsoximetry ear sensor structure according to claim 1 wherein the sensor element is mounted toward an end of each leg, the rib is located on a side of the web facing the sensor element, the rib having an upper edge forming a crescent when the ends of the legs are normally urged toward each other.

12. Pulsoximetry ear sensor structure according to claim 11 wherein the rib, web, legs and upper edge are constructed and arranged so that when the legs are spread apart by a maximum amount the upper edge of the rib is substantially parallel to the web.

13. Pulsoximetry ear sensor structure comprising a one-piece, elastic plastic support for a sensor element, the support including a pair of legs that are normally urged toward each other and selectively spread apart, the legs extending in a longitudinal direction, the sensor element being mounted toward an end of each leg, the legs being interconnected to each other by an elastically deformable web that extends in a longitudinal direction generally between the legs, the web having a surface and at least one elastically deformable rib extending in the web longitudinal direction and projecting from the web surface in the same general direction as the direction in which the legs extend so that the rib and the web tend to urge the legs in a direction at a right angle to the direction of extent of the legs so that the ends of the legs including the sensor element are normally biased toward each other so they can abut opposite faces of an ear of a subject.

* * * * *